(12) United States Patent
Guo et al.

(10) Patent No.: US 12,029,414 B2
(45) Date of Patent: Jul. 9, 2024

(54) MINIMALLY INVASIVE SURGICAL SUTURE END LOCKING DEVICE, METHOD AND OPERATING GUN

(71) Applicant: JIANGSU TECH-BIO-MED MEDICAL EQUIPMENT CO., LTD., Changzhou (CN)

(72) Inventors: Yanlin Guo, Changzhou (CN); Wei Zhang, Changzhou (CN)

(73) Assignee: JIANGSU TECH-BIO-MED MEDICAL EQUIPMENT CO., LTD., Jiangsu (CN)

(*) Notice: Subject to any disclaimer, the term of this patent is extended or adjusted under 35 U.S.C. 154(b) by 213 days.

(21) Appl. No.: 17/900,837

(22) Filed: Aug. 31, 2022

(65) Prior Publication Data

US 2023/0225727 A1 Jul. 20, 2023

Related U.S. Application Data

(63) Continuation of application No. PCT/CN2022/084310, filed on Mar. 31, 2022.

(30) Foreign Application Priority Data

Jan. 19, 2022 (CN) .......................... 202210060732.4

(51) Int. Cl.
*A61B 17/04* (2006.01)
(52) U.S. Cl.
CPC ...... *A61B 17/0487* (2013.01); *A61B 17/0469* (2013.01); *A61B 17/0485* (2013.01); *A61B 2017/0488* (2013.01)

(58) Field of Classification Search
CPC ............ A61B 17/0487; A61B 17/0469; A61B 17/0485; A61B 2017/0488
See application file for complete search history.

(56) References Cited

U.S. PATENT DOCUMENTS

| | | | | |
|---|---|---|---|---|
| 6,086,608 A | * | 7/2000 | Ek | A61B 17/0487 606/301 |
| 6,200,329 B1 | * | 3/2001 | Fung | A61B 17/0487 606/232 |

(Continued)

FOREIGN PATENT DOCUMENTS

| | | |
|---|---|---|
| CN | 1853578 A | 11/2006 |
| CN | 202892020 U | 4/2013 |

(Continued)

*Primary Examiner* — Phong Son H Dang
(74) *Attorney, Agent, or Firm* — SZDC Law PC

(57) ABSTRACT

A minimally invasive surgical suture end locking device includes a hooking assembly, a clamping structure, a power rod and an external conduit. The hooking assembly includes an annular structure enclosed by a flexible material and a force application end, the clamping structure is configured to press the locking pin, the power rod is configured to press the clamping structure by linear motion, and the external conduit is provided with a through hole, the through hole being provided on the side of a position where the clamping structure and the power rod contact each other for a portion of the suture passing through the through area to be led out. There is provided in the present invention a device that allows to tighten and lock the suture directly at the end proximal to the position where the suture is led out from the human tissue.

18 Claims, 13 Drawing Sheets

(56) References Cited

U.S. PATENT DOCUMENTS

| | | | |
|---|---|---|---|
| 8,398,680 B2* | 3/2013 | Sauer | A61B 17/0487 |
| | | | 606/232 |
| 9,642,616 B2* | 5/2017 | Nobles | A61B 17/0485 |
| 10,016,193 B2* | 7/2018 | Smith | A61B 17/0469 |
| 10,603,027 B2* | 3/2020 | Sauer | A61B 17/0401 |
| 11,219,447 B2* | 1/2022 | Juan | A61B 17/0467 |
| 2003/0167062 A1* | 9/2003 | Gambale | A61B 17/0487 |
| | | | 606/148 |
| 2003/0204205 A1* | 10/2003 | Sauer | A61B 1/0014 |
| | | | 606/232 |
| 2008/0234729 A1* | 9/2008 | Page | A61B 17/0487 |
| | | | 606/232 |
| 2011/0071546 A1 | 3/2011 | Jakoubek | |
| 2017/0209135 A1 | 7/2017 | Sullivan et al. | |
| 2017/0301124 A1 | 10/2017 | Dala-Krishna | |

FOREIGN PATENT DOCUMENTS

| | | |
|---|---|---|
| CN | 204723113 U | 10/2015 |
| CN | 109730734 A | 5/2019 |
| CN | 110575210 A | 12/2019 |
| CN | 111358509 A | 7/2020 |
| CN | 112244910 A | 1/2021 |
| CN | 113040843 A | 6/2021 |
| CN | 114073554 A | 2/2022 |
| EP | 2116194 A1 | 11/2009 |

* cited by examiner (a)

(b)

(c)

(d)

MINIMALLY INVASIVE SURGICAL SUTURE END LOCKING DEVICE, METHOD AND OPERATING GUN

This application is a Continuation Application of PCT/CN2022/084310, filed on Mar. 31, 2022, which claims priority to Chinese Patent Application No. 202210060732.4, filed on Jan. 19, 2022, which is incorporated by reference for all purposes as if fully set forth herein.

TECHNICAL FIELD

The present invention relates to the technical field of medical devices, in particular to a minimally invasive surgical suture end locking device, method and operating gun.

BACKGROUND

In current minimally invasive surgery and interventional procedures, an incision is made in the patient's body to allow for the insertion of instruments such as endoscopes or interventional catheters into the body, and the suturing of tissues and fixation of the suture end are completed in the patient's body.

As far as the fixation of the suture end is concerned, it is common to subject the end to multiple knotting and locking, i.e., knotting the suture end for multiple times for locking inside the patient's body with the relevant instruments, in order to avoid subsequent loosening. However, after the surgery, it is difficult to eliminate the loosening of the suture due to the movement of the tissues during the life activities and due to the material of the suture.

In order to solve these problems, some manufacturers have developed a locking device that locks the suture end by means of a locking pin. Specifically, the suture end is clamped through elastic deformation of the locking pin, and the deformed pin is attached to the surface of the human tissue to prevent the loosening of the suture.

When the suture is tightened by the existing locking device to ensure the effectiveness of the suturing, a structure arranged outside the human body that can be used to tighten the suture is required. In this way, the travel of the suture is relatively long, making it difficult to control the actual required suture tension after suturing because the suture is stretched over a relatively large distance.

SUMMARY

The present invention provides a minimally invasive surgical suture end locking device, which can effectively solve the problems discussed in the background section. Also, the present invention provides a minimally invasive surgical suture end locking method and a minimally invasive surgical suture end locking operating gun with the same technical effects.

To this end, the present invention adopts technical solutions described below.

A minimally invasive surgical suture end locking device for clamping and securing the end of a suture by means of a locking pin, comprising: a hooking assembly, a clamping structure, a power rod and an external conduit;

wherein the hooking assembly comprises an annular structure enclosed by a flexible material and a force application end leading out relative to the annular structure, wherein the annular structure is configured to lead out from a through area of the locking pin with a lead-out portion forming a closed area, and wherein the force application end is configured to drive the suture entering the closed area partially through the through area by pulling the annular structure under the action of an external force in the human body;

wherein the clamping structure is configured to press the locking pin so that the locking pin deforms and clamps the suture, and wherein the power rod is provided with a pressing portion to press the clamping structure by linear motion so that the clamping structure moves and completes the pressing action; and wherein the clamping structure and the power rod are disposed in the external conduit, wherein the locking pin is inserted from an end of the external conduit and the depth of insertion is limited by a stop structure provided on the locking pin, and wherein the external conduit is provided with a through hole through which a portion of the suture passing through the through area is led out by the pulling of the annular structure, the through hole being provided on the side of a position where the clamping structure and the power rod contact each other at a set distance from the contact position.

Further, the through hole is a straight hole and extends along the linear movement direction of the power rod.

Further, the force application end is a hook structure.

Further, the power rod is provided with a cutting portion at an end thereof, wherein the cutting portion approaches one sidewall of the through hole along with the pressing movement of the power rod until it reaches a close enough distance with respect to the one sidewall of the through hole and continues to approach, the cutting portion thus cutting the suture passing through the through hole by cooperating with the edge of the sidewall.

Further, the external conduit comprises a guide seat mounted at an end thereof, wherein the guide seat is configured to limit the insertion depth of the locking pin and guide the movement of the clamping structure.

Further, the movement of the clamping structure is perpendicular to the direction of insertion of the locking pin into the guide seat.

Further, the guide seat is provided with a guide groove, and the clamping structure is provided with a protruding portion moving along the guide groove.

Further, the clamping structure is provided with at least one raised structure facing the locking pin for partially pressing the locking pin.

Further, the pressing portion comprises a slope for pressing the clamping structure, wherein an end of the slope forms a sharp structure that can be inserted into a gap between the clamping structure and the inner wall of the external conduit, and wherein the slope is inclined relative to the direction in which the guide seat guides the clamping structure.

A minimally invasive surgical suture end locking method using the minimally invasive surgical suture end locking device described above, comprising the following steps of:
 installing the hooking assembly in place relative to the locking pin and installing the locking pin in place relative to the external conduit, and extending the hooking assembly and the locking pin into a designated position within the human body;
 pulling the end of suture after suturing is complete so that the end of suture enters the closed area;

pulling the force application end and controlling the end of suture so that the suture partially penetrates the through area with a preset range of tension being maintained;

controlling the external conduit to press the locking pin against the surface of the human tissue;

providing pressing power to the clamping structure through the power rod to enable the locking pin to clamp the suture; and cutting the suture and removing from the human body the hooking assembly separated from the suture, excess suture and the locking device.

Further, controlling the end of suture includes pulling the suture end on the side of the locking pin proximate to the sutured tissue such that during the pulling of the force application end, the suture deviating from the end overlaps and penetrates through the through area of the locking pin.

Further, controlling the end of suture includes pulling the force application end to drive the suture end through the through area of the locking pin by the annular structure, and pulling the suture end on the side of the locking pin away from the sutured tissue.

A minimally invasive surgical suture end locking operating gun, comprising the minimally invasive surgical suture end locking device described above and an operating assembly disposed outside the human body for operation, wherein the operating assembly comprises two half-shells assembled to in a docking manner to form a cavity, and a force application handle partially disposed within the cavity and rotatably connected to the half-shells;

wherein one end of the force application handle located within the cavity is slidably connected to the power rod, wherein the outer cross-section of the external conduit is a cylinder having an axis fixed relative to the half-shells, and wherein the force application handle presses the power rod during rotation.

Further, an end of the power rod is provided with a connection structure slidably connected to the force application handle, the connection structure comprising:

a first stop and a second stop provided side by side along the length of the power rod, the first stop and the second stop being connected to each other by a connecting rod, the first stop being relatively close to the minimally invasive surgical suture end locking device;

wherein the force application handle is provided with a recess at an end thereof to accommodate the connecting rod, the end of the force application handle being affixed to the first stop and second stop, respectively.

Further, the first stop is in contact with the force application handle by means of a spherical surface, and the force application handle is correspondingly provided with a curved surface that is curved in the same direction to fit with the spherical surface.

Further, the force application handle is in contact with the second stop by means of a curved surface.

Further, the operating gun further comprises a rotating structure having a first end jacketed on the external conduit and located outside the cavity and fixedly connected to the external conduit, and a second end jacketed on the power rod and located inside the cavity and driving the power rod to rotate.

Further, a snap slot is provided between the first end and the second end for accommodating a partial edge of the half-shells.

Further, the second end is affixed to the power rod through a prismatic through hole to realize transmission of rotational power.

Further, the operating gun further comprises a sensing structure comprising a rod body leading out from the force application handle, and a stepped seat disposed on the inner wall of the cavity and having a plurality of stepped structures;

wherein the rod body is arranged against the stepped seat, so that it sequentially reaches different stepped structures on the stepped seat during rotation of the force application handle, creating a jamming feeling which is transmitted to the operator through the force application handle.

With the technical solutions of the present invention, the following technical effects can be achieved.

There is provided in the present invention a device that allows to tighten and lock the suture directly at the end proximal to the position where the suture is led out from the human tissue, which makes it easier to control the degree of tightness of the suture on the tissue as opposed to tightening the suture by pulling the suture out of the body through the entire locking device, alleviating the difficulty of control caused by the long travel of the suture and its elasticity. The present invention also provides a minimally invasive surgical suture end locking method and an operating gun that can obtain the same technical effects by applying the above-mentioned device.

DESCRIPTION OF THE DRAWINGS

In order to more clearly illustrate the embodiments of the present invention or the technical solutions in the prior art, the accompanying drawings to be used in the description of the embodiments or prior art will be briefly described below. It is obvious that the accompanying drawings in the following description are only some of the embodiments recorded in the present invention, and other accompanying drawings can be obtained according to these accompanying drawings without creative work for those of ordinary skill in the art.

REFERENCE SIGNS

Figure 1:
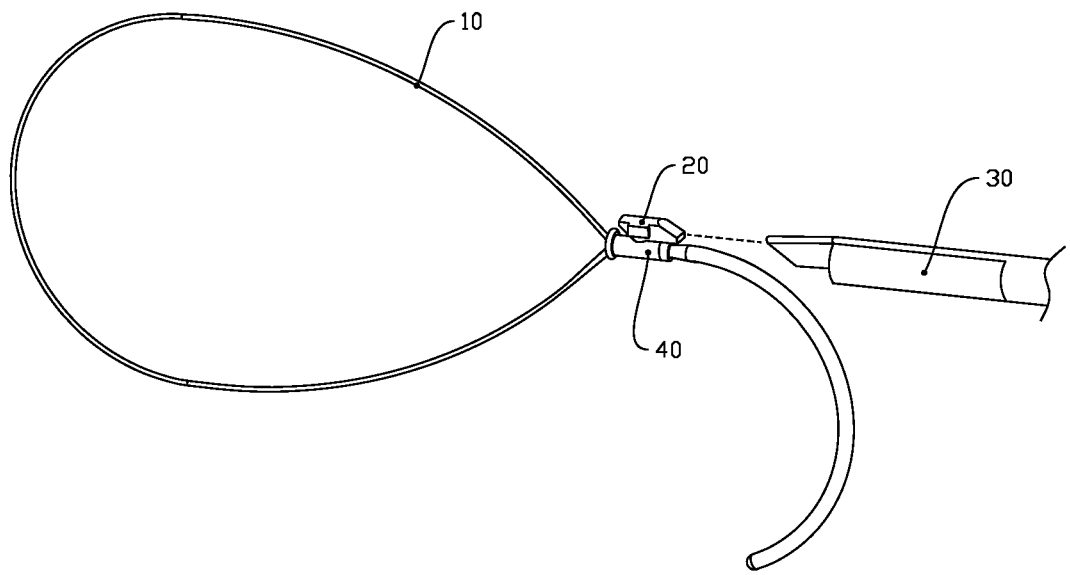
FIG. 1 is a schematic structural diagram of a minimally invasive surgical suture end locking device except for the external conduit.
Figure 2:
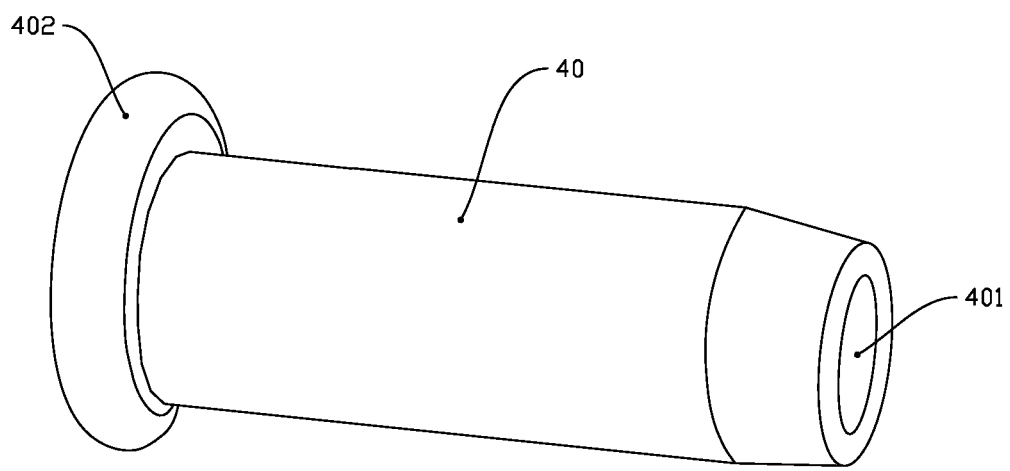
FIG. 2 is a schematic structural diagram of the locking pin.

10. Hooking assembly;
101. Annular structure;
102. force application end;
103. Support buckle;
20. Clamping structure;
201. Protruding portion;
202. Convex structure;
203. Guide surface;
204. First clamping structure;
204a. Hole;
205. Second clamping structure;
30. Power rod;
301. Pressing portion;
3011. Slope surface;
302. Cutting portion;
303. Connecting structure;
3031. First stop;
3032. Second stop;
3033. Connecting rod;
40. Locking pin;
401. Through area;
402. Stop structure;
50. Suture;
501. End;
502. End leading out from tissue;
60. External conduit;
601. Through hole;
602. Guide seat;
6021. Guide groove;
603. Plug;
70. Operating assembly;
701. Half shell;
702. force application handle;
7021. Recess;
7022. Rod body;
703. Stepped seat;
80. Rotating structure;
801. First end;
802. Second end.

DETAILED DESCRIPTION

The technical solutions in the embodiments of the present invention will be described clearly and completely in conjunction with the accompanying drawings in the embodiments of the present invention. Obviously, the described embodiments are only a part of the embodiments of the present invention, rather than all the embodiments.

Unless otherwise defined, all technical and scientific terms used herein have the same meaning as commonly understood by those skilled in the art of the present invention. The terms used herein are for the purpose of describing specific embodiments only and are not intended to limit the invention. The term "and/or" as used herein includes any and all combinations of one or more of the related listed items.

FIGS. 1-6 illustrate a minimally invasive surgical suture end locking device for clamping and securing the end of a suture 50 by means of a locking pin 40, comprising: a hooking assembly 10, a clamping structure 20, a power rod 30 and an external conduit 60, wherein the hooking assembly 10 comprises an annular structure 101 enclosed by a flexible material and a force application end 102 leading out relative to the annular structure 101, wherein the annular structure 101 is configured to lead out from a through area 401 of the locking pin 40 with a lead-out portion forming a closed area, and wherein the force application end 102 is configured to drive the suture 50 entering the closed area partially through the through area 401 by pulling the annular structure 101 under the action of an external force in the human body; wherein the clamping structure 20 is configured to press the locking pin 40 so that the locking pin 40 deforms and clamps the suture 50, and wherein the power rod 30 is provided with a pressing portion 301 to press the clamping structure 20 by linear motion so that the clamping structure 20 moves and completes the pressing action; and wherein the clamping structure 20 and the power rod 30 are disposed in the external conduit 60, wherein the locking pin 40 is inserted from an end of the external conduit 60 and the depth of insertion is limited by a stop structure 402 provided on an end of the locking pin, and wherein the external conduit 60 is provided with a through hole 601 through which a portion of the suture 50 passing through the through area 401 is led out by the pulling of the annular structure 101, the through hole 601 being provided on the side of a position where the clamping structure 20 and the power rod 30 contact each other at a set distance from the contact position.

There is provided in the present invention a device that allows to tighten and lock the suture 50 directly at the end proximal to the position where the suture is led out from the human tissue, which makes it easier to control the degree of tightness of the suture 50 on the tissue as opposed to tightening the suture by pulling the suture out of the body through the entire locking device, alleviating the difficulty of control caused by the long travel of the suture 50 and its elasticity.

Figure 3:
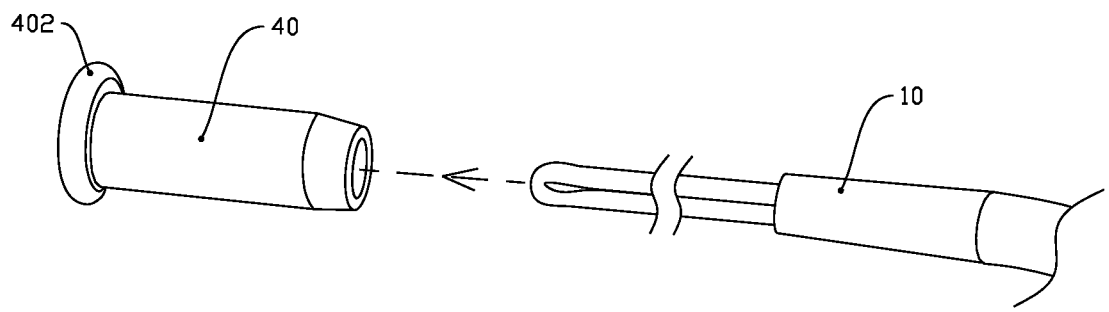
FIG. 3 is a schematic diagram of inserting the annular structure of the hooking assembly into the through area of the lock pin.
Figure 4:
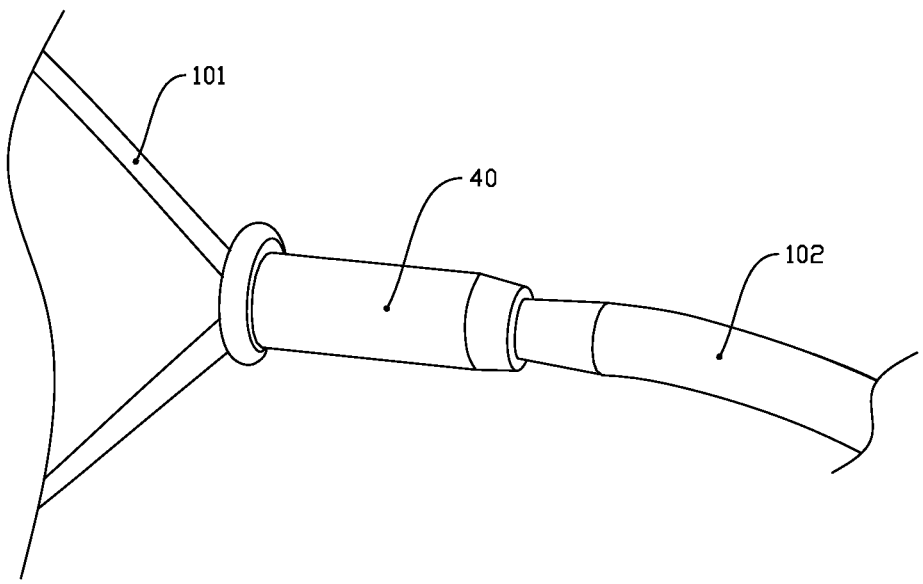
FIG. 4 is a schematic diagram after the insertion process is completed in FIG. 3.

The connection of the annular structure 101 and the force application end 102 is preferably done in advance, so as to participate in the subsequent operation as a whole consumable. The connection of the locking pin 40 with respect to the external conduit 60 is preferably done after the connection with the hooking assembly 10 is completed. The connection of the hooking assembly 10 with the locking pin 40, as shown in FIGS. 3 and 4, can be easily done by inserting the annular structure 101 into the through area 401 of the locking pin 40. The force application end 102 can be inserted into the external conduit 60 and lead out through the through hole 601 before the locking pin 40 is inserted into the external conduit 60, and then the locking pin 40 is inserted into the external conduit 60, followed by fine adjustment of the position of the annular structure 101 and the force application end 102 relative to the locking pin 40. The above connection process of the respective structures is a specific embodiment convenient for assembly and field use, and other connection processes that can obtain the final use state are also within the scope of protection of the present invention.

Figure 5:
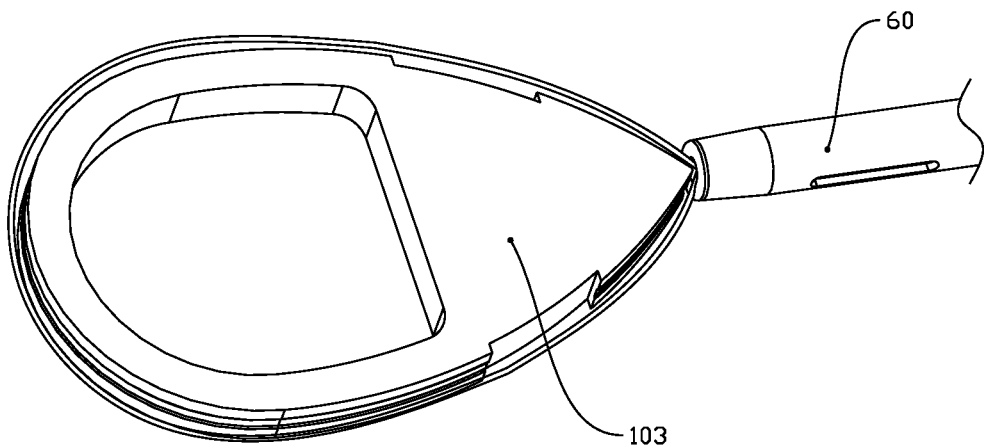
FIG. 5 is a schematic diagram of the installation of the support buckle.

The product connected as above may be considered as ready for delivery. The product may be placed in a clean and airtight package and can be used directly after unpacking. To prevent the hooking assembly 10 from falling off during transportation and during the process of entering the human body, as shown in FIG. 5, a support buckle 103 may be provided to support the annular structure 101 leading out from the locking pin 40. Of course, the support here preferably makes the annular structure 101 obtain a certain elastic expansion so as to ensure a tight fit with the support buckle 103, or other structures such as a slot may be provided on the support buckle 103 to receive the annular structure 101. The support buckle 103 can be removed before use.

Figure 6:
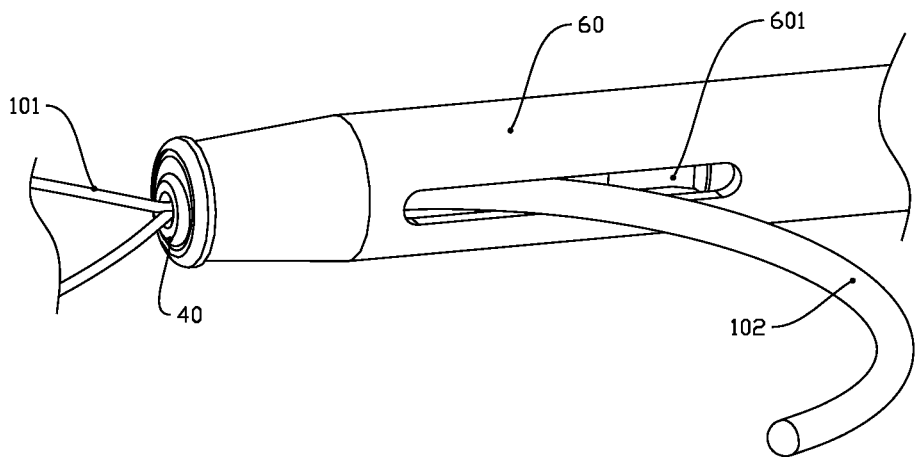
FIG. 6 is a schematic diagram of the hooking assembly and locking pin after installation is completed relative to the external conduit.

In order to reduce the difficulty of connection and installation of the above structures, as shown in FIG. 6, the through hole 601 is a straight hole extending along the direction of linear movement of the power rod 30, thus making easier the process of determining the position of the hooking assembly 10 relative to the outer conduit 60. Especially for the process of the force application end 102 passing through the through hole 601, a larger space is obtained.

As a preferred structural form of the force application end 102 to facilitate in vivo operation, based on the above objectives and as a preferred embodiment, as shown in FIGS. 1 and 6, the force application end 102 adopts a hook structure, which makes it easier to apply force to it with existing instruments and is easy to machine.

In order to reduce the operation steps and shorten the operation time, the structural form of the power rod 30 is optimized, specifically, an end of the power rod 30 is provided with a cutting portion 302. The cutting portion 302 approaches one sidewall of the through hole 601 along with the pressing movement of the power rod 30 until it reaches a close enough distance with respect to the one sidewall of the through hole 601 and continues to approach, the cutting portion 302 thus cutting the suture 50 passing through the through hole 601 by cooperating with the edge of the sidewall.

The cutting portion 302 can be directly shaped during the processing of the power rod 30, and the pressing portion 301 can be obtained in the same way, so that the power rod 30 as a whole can ensure better stability in the process of power supply and cutting, and is more robust and durable, making the installation of the product less difficult.

Figure 7:
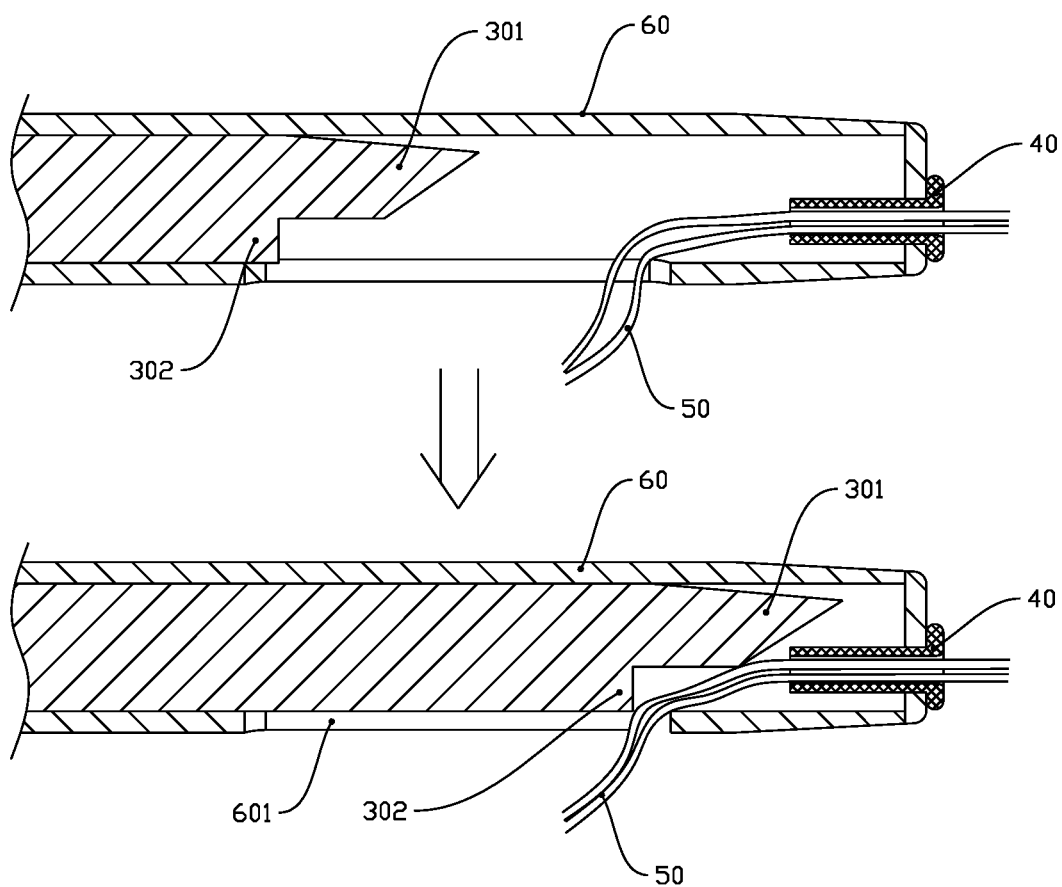
FIG. 7 is a schematic diagram of the process of cutting the suture by the cutting portion.

As shown in FIG. 7, the cutting action of the cutting portion 302 is carried out in parallel with the power rod 30 pressing the clamping structure 20, which can completely omit an independent step of cutting the suture 50. Before pressing and cutting, it is necessary to ensure that the suture 50 is stretched properly. As the cutting portion 302 approaches one sidewall of the through hole 601, the cutting portion 302 and the sidewall of the through hole 601 form a near double-edged structure. For the suture 50 passing between the two edges, when the pressing pressure between the edges reaches a certain value and the suture 50 acquires a certain tension, the purpose of cutting is more easily achieved.

Figure 8:
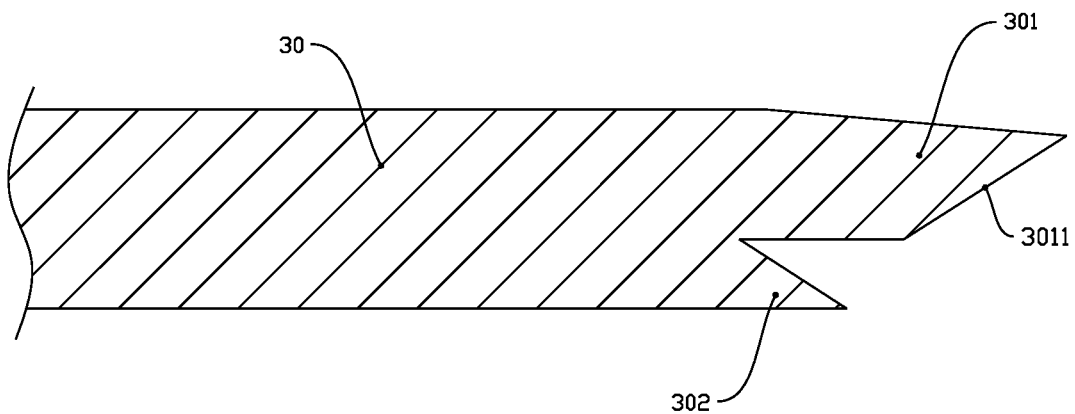
FIG. 8 is a sectional view of the end of the power rod.

In order to improve the cutting effects, the shape of the cutting portion 302 can be optimized to control the sharpness of the cutting edge provided by it. The power rod 30 is installed inside the external conduit 60 and will not cause any impact on the patient. There is more room for improvement compared to the improvement of the sidewall of the through hole 601. Referring to FIG. 8, the shape of the cutting portion, which is located at the end of the power rod 30, can be controlled by the subsequent machining process.

Figure 9:
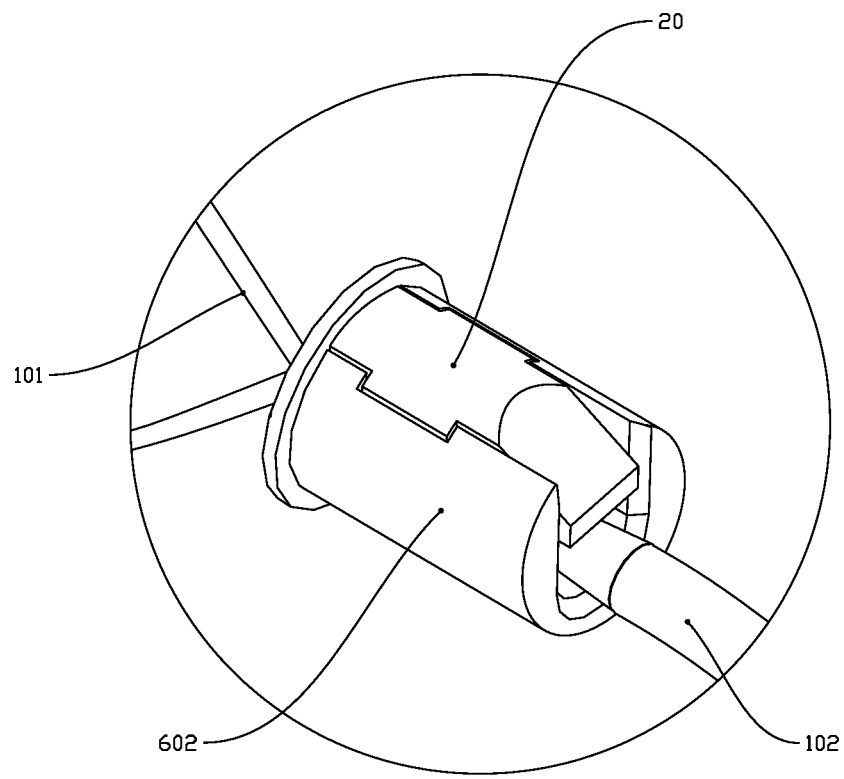
FIG. 9 is a schematic diagram of the installation of the guide seat relative to the hooking assembly and the clamping structure.

In practical application, one side of the external conduit 60 extends into the human body and the other side is located outside the human body, so the length is relatively large and it is difficult to directly install the clamping structure 20 at its end. To solve this problem, as an optimized embodiment and as shown in FIG. 9, the external conduit 60 further includes a guide seat 602 installed at the end thereof, the guide seat 602 is configured to limit the insertion depth of the locking pin 40 and guide the movement of the clamping structure 20. When the guide seat 602 is separated from the external conduit 60, the clamping structure 20 can be installed, and after the installation is completed, it can be directly installed as a whole. The guide function here can achieve the relative fixation of the clamping structure 20 in a narrow space, and accurately limit the direction of its movement.

During the operation, in addition to meeting the installation needs of the locking pin 40, a possibly smaller external dimensions of the external conduit 60 is more preferable for the patient. For this purpose, it is more desirable that the clamping structure 20 imparts a greater degree of compression on the locking pin 40 through a smaller range of motion, and for this purpose, the movement of the clamping structure 20 is perpendicular to the direction of insertion of the locking pin 40 into the guide seat 602.

Figure 10:
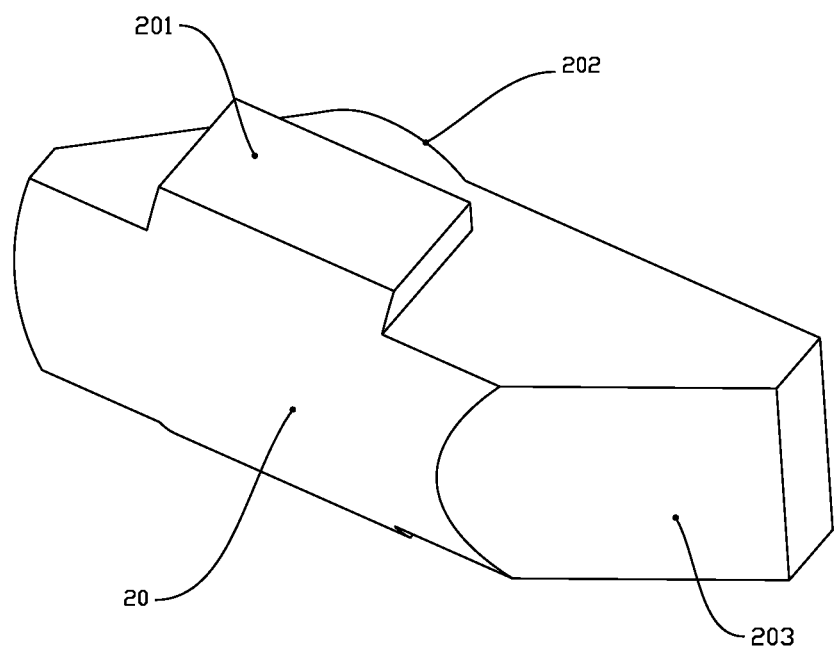
FIG. 10 is a schematic diagram of one structure of the clamping structure.
Figure 11:
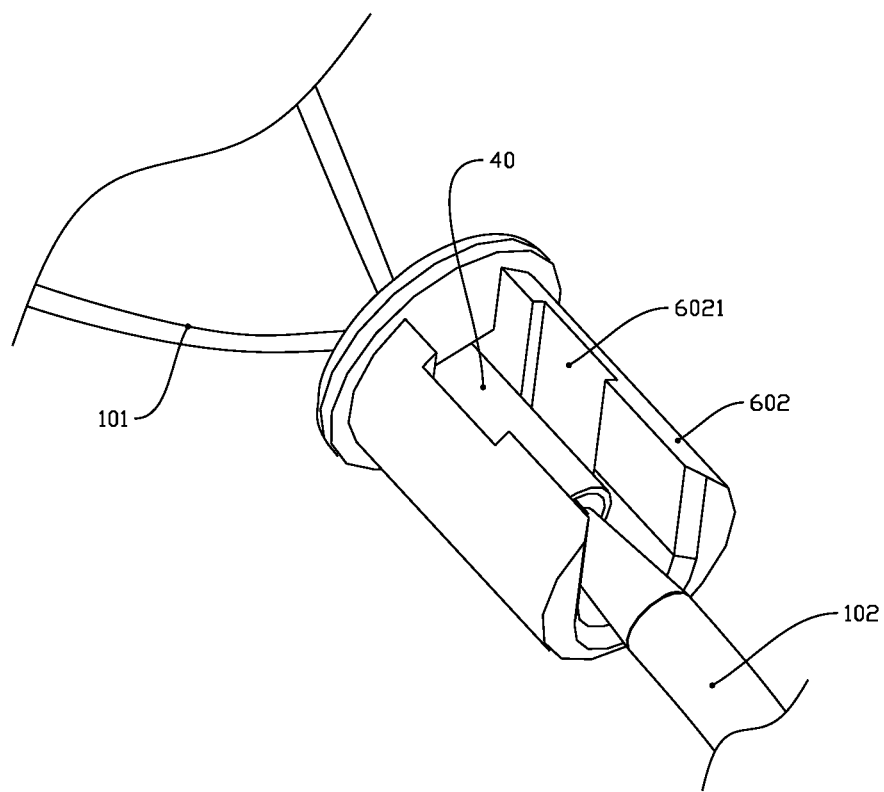
FIG. 11 is a schematic diagram of the installation of the guide seat relative to the hooking assembly.
Figure 12:
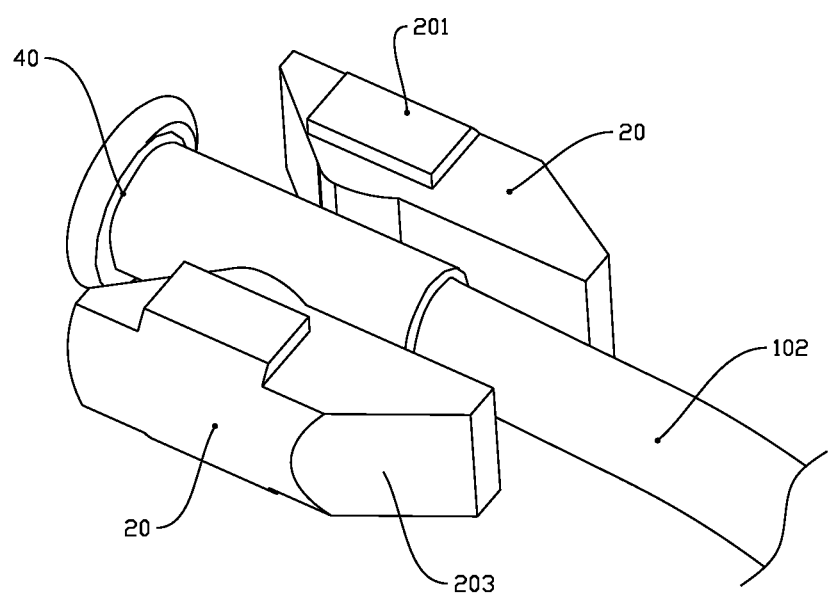
FIG. 12 is a schematic diagram of the position of the two clamping structures relative to the locking pin.

As a specific way of guiding, as shown in FIGS. 9 to 11, the guide seat 602 is provided with a guide groove 6021, and the clamping structure 20 is provided with a protruding portion 201 that moves along the guide groove 6021. This is a most convenient implementation and the guidance is stable. In the present invention, the number of clamping structures 20 is selected comprehensively considering the installation space in the external conduit 60, the shape of the power rod 30, etc. FIG. 12 shows two clamping structures 20. Correspondingly, it is sufficient to provide two pressing portions 301 at the end of the power rod 30.

Figure 13:
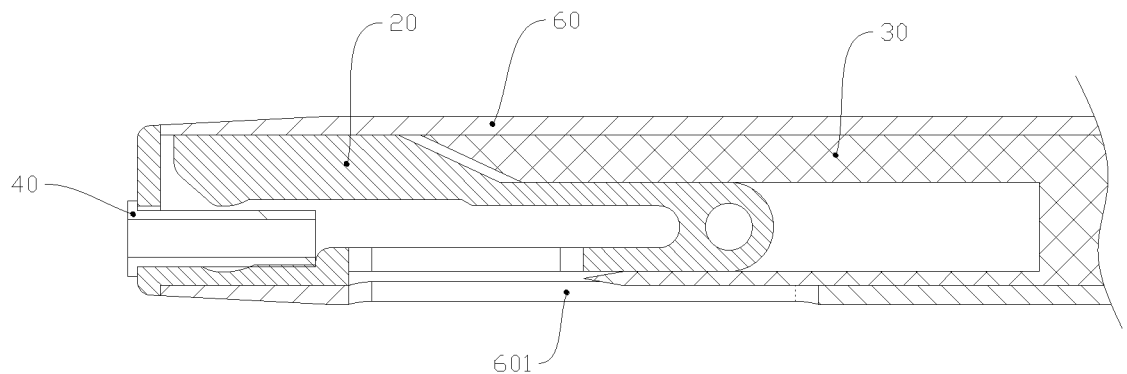
FIG. 13 is a cross-sectional view of the installation position of the clamping structure in an optimized manner.
Figure 14:
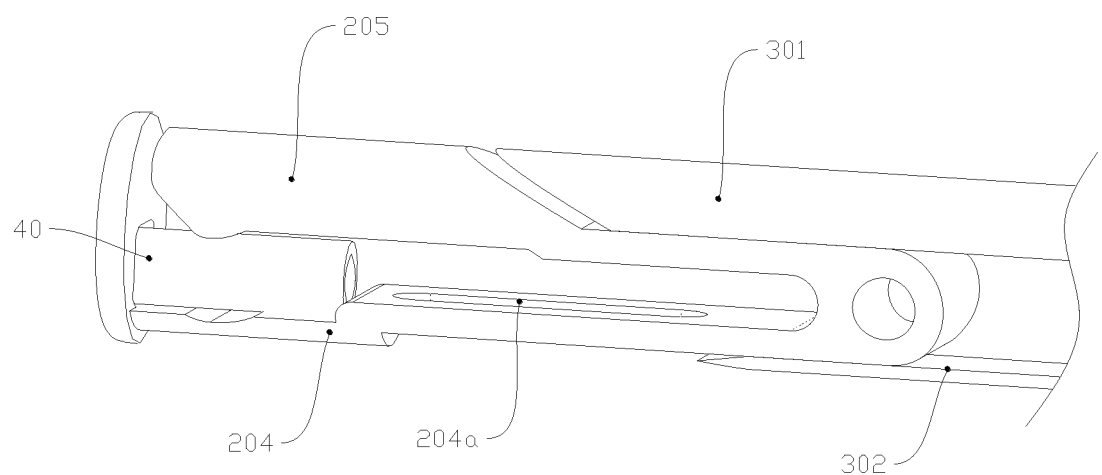
FIG. 14 is a schematic diagram of the installation of the clamping structure in the optimized manner.

Alternatively, as another embodiment of the clamping structure 20, the clamping structure 20 is configured in the form of a V-shaped clamp, as shown in FIGS. 13 and 14. Here, the V-shaped clamp specifically includes a first clamping structure 204 and a second clamping structure 205 arranged at a preset angle. When the first clamping structure 204 is fixedly arranged, the second clamping structure 205 can move close to the first clamping structure 204 through its own elastic deformation under the pressing of the power rod 30, or through an elastic change in angle relative to the first clamping structure 204, or through both of the above. When the pressing force is removed, the elastic reset can be realized.

When the clamping structure 20 of this structural form is adopted, the purpose of pressing and deforming the locking pin can be achieved simply by placing the locking pin 40 between the two clamping structures at the desired clamping position. In this structural form, extending the length of the first clamping structure 204 and the second clamping structure 205 as much as possible can make the above-mentioned elastic change easier. For this purpose, a recessed area for partial accommodation of the clamping structure 20 may be provided at the end of the power rod 30 to accommodate the extension of length.

Figure 15:
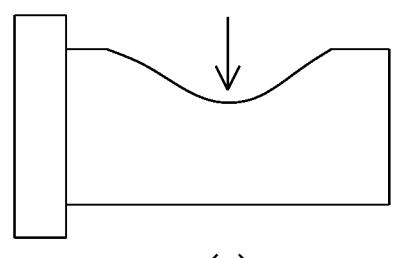
FIG. 15(a) to (d) are schematic diagrams of the four concentrated force positions of the locking pin.
Figure 15:
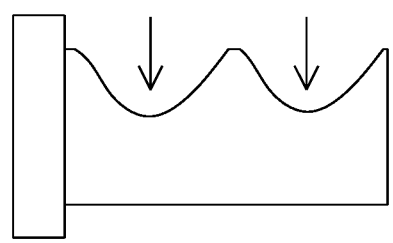
Figure 15:
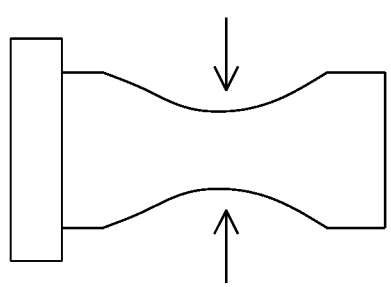
Figure 15:
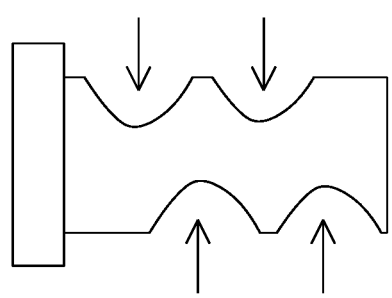

As a more optimized form of the clamping structure 20 in this structural form, the clamping structure 20 may be integrally formed with a plug 603 used to block the end of the external conduit 60, thereby further reducing the difficulty of installation. Specifically, the plug 603 may be connected to the first clamping structure 204. To impart larger strength to the first clamping structure 204, it may be provided with a stepped structure, so that the locking pin 40 can be further positioned through the stepped surface while the strength is improved. Other shape forms that meet the space requirements are also within the scope of protection of the present invention. Since the clamping structure 20 of this structural form occupies a large area in the external conduit 60, it may significantly affect the leading out of the suture from the through hole 601. In order to solve this problem, the first clamping structure 204 may be provided with a hole 204*a* corresponding to the through hole 601, thus avoiding the occurrence of interference. In practice, even if the suture 50 is clamped and fixed by the locking pin 40, there is still a risk that it may fall off during the subsequent continuous movement of the human tissue. To minimize such risk, the clamping structure 20 may be provided with at least one raised structure 202 facing the locking pin 40 and partially pressing the locking pin 40. Compared with flatting the locking pin 40 as a whole, the pressing of the locking pin 40 by the raised structure 202 can form a more concentrated pressing position for the suture 50, such as the position indicated by the arrow in FIG. 15, that is, the position where the suture 50 obtains centralized pressing. FIG. 15(*a*) shows the position of the force on the locking pin 40 that ensures stable fixation of the suture 50 by a concentrated pressing. Of course, in addition to the centralized pressing position, other positions of the locking pin 40 can be deformed by means of flattening, so as to obtain a slightly smaller pressing force compared to the centralized pressing position. FIG. 15(*b*) shows the position of the force on the locking pin 40 when the clamping structure 20 is provided with more than one, specifically two raised structures 202, which function in the same way as FIG. 15(*a*) and, of course, provide better fixation of the suture 50, but will appropriately increase the machining difficulty of the clamping structure 20. FIG. 15(*c*) shows the position of the force on the locking pin 40 when two clamping structures 20 are provided and each clamping structure 20 is provided with one raised structure 202 to press the locking pin 40. FIG. 15(*d*) shows the position of the force on the locking pin 40 when two clamping structures 20 are provided and each clamping structure 20 is provided with more than one, specifically two raised structures 202. In such configuration, it is preferred that the raised structures 202 on the two clamping structures 20 are staggered, as shown in the figure, so that the pressed locking pin 40 obtains a final shape that is approximately wavy, which provides better fixation of the suture 50. The above solutions can be selected according to actual needs. In the implementation, in addition to the raised structure 202, a corresponding recessed area can be provided. The area pressed and deformed due to the raised structure 202 can be deformed into the recessed area, as shown in FIG. 13, which shows how the recessed area can be provided. Specifically, the recessed area may be a part of the clamping structure 20, or a part of the external conduit 60.

As a preferred embodiment, see FIG. 8, the pressing portion 301 includes a slope 3011 for pressing the clamping structure 20, wherein the end of the slope 3011 forms a sharp structure that can be inserted into a gap between the clamping structure 20 and the inner wall of the external conduit 60, and wherein the slope 3011 is inclined relative to the direction in which the guide seat 602 guides the clamping structure 20. The slope 3011 is provided to translate the linear motion of the power rod 30 into the linear motion of the clamping structure 20, achieving the change of direction.

Figure 16:
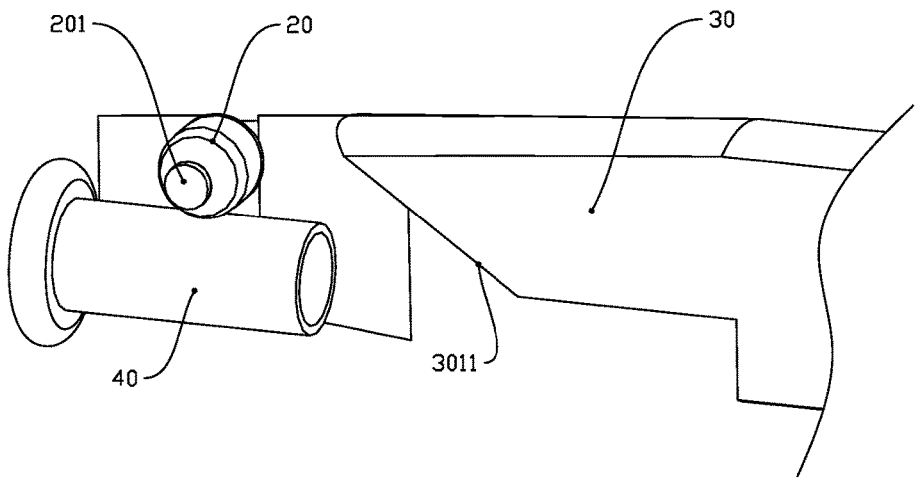
FIG. 16 is a schematic diagram of the installation of another clamping structure.

As shown in FIG. 10, the clamping structure 20 may be provided with a guide surface 203 corresponding to the slope 3011 in order to accommodate mutual pressing with the pressing portion 301, or, as shown in FIG. 16, the clamping structure 20 may be directly provided as a shaft body structure or a structure having a partially curved surface, so as to produce mutual pressing with the slope 3011 through the curved surface.

Figure 17:
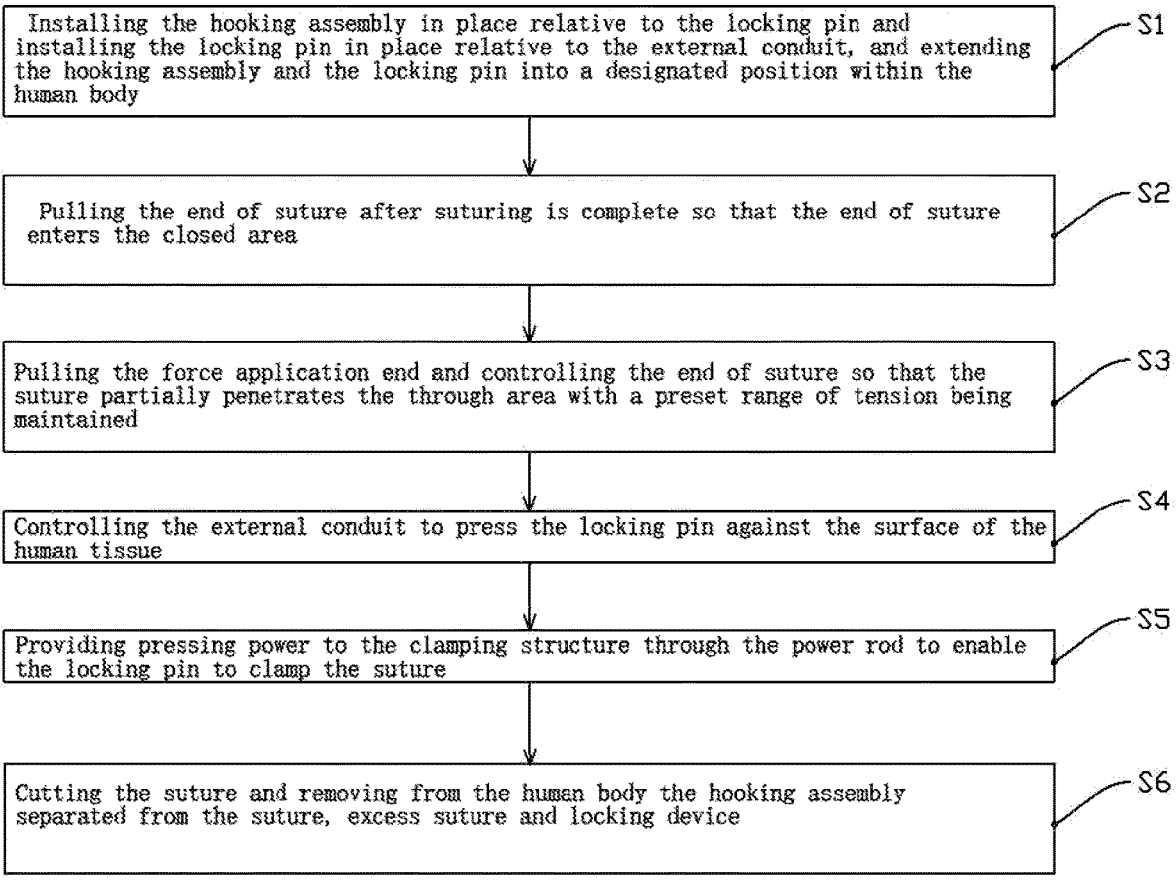
FIG. 17 is a flow diagram of a minimally invasive surgical suture end locking method.
Figure 18:
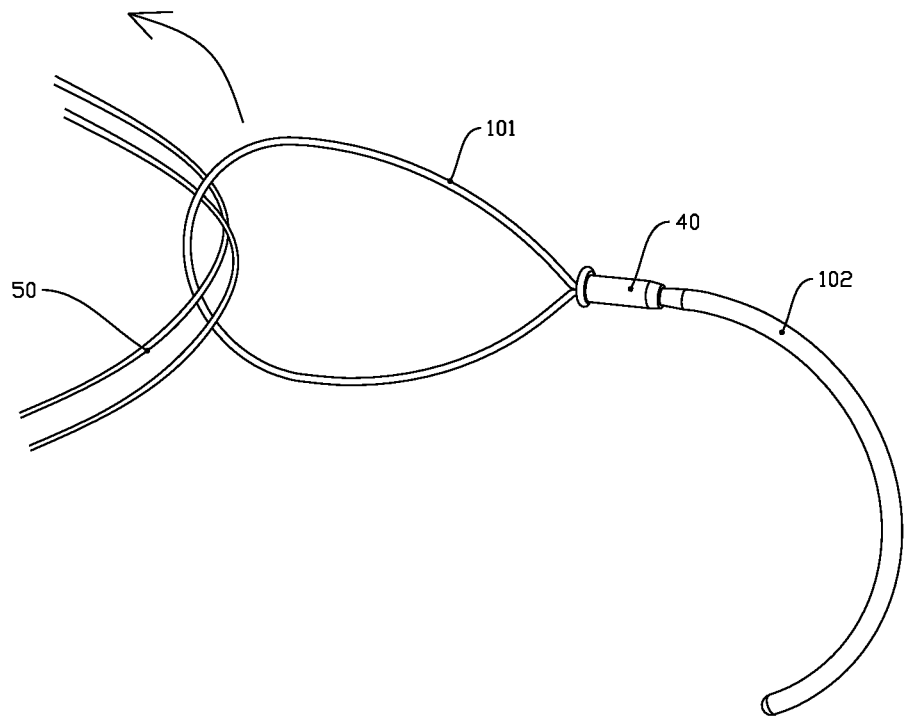
FIG. 18 is a schematic diagram of the end of a suture entering within a closed area.

As a locking method of the above-described minimally invasive surgical suture end locking device, specific reference can be made to the following steps so as to achieve optimal effects. As shown in FIG. 17, there is provided a minimally invasive surgical suture end locking method using the minimally invasive surgical suture end locking device as described above, comprising the following steps of:

S1: installing the hooking assembly 10 in place relative to the locking pin 40 and installing the locking pin 40 in place relative to the external conduit 60, and extending the hooking assembly and the locking pin into a designated position within the human body, as shown in FIGS. 3, 4 and 6, and in a manner as in the embodiment described above, ensuring that the closed area is formed and that the locking pin 40 is in place relative to the clamping structure 20;

S2: pulling the end of suture 50 after suturing is complete so that the end of suture 50 enters the closed area, as shown in FIG. 18, thereby enabling the movement of the annular structure 101 to be transmitted towards the suture 50;

S3: pulling the force application end 102 and controlling the end of suture 50 so that the suture 50 partially penetrates the through area with a present range of tension being maintained, wherein the purpose of pulling the force application end 102 is to drive the suture 50 into and pass through the through area 401 of the locking pin 40 so as to achieve the purpose of pressing and fixing the suture, and the purpose of controlling the end of suture 50 is to avoid loosening of the suture 50 during the operation, which may affect the effectiveness of the tissue suturing;

S4: controlling the external conduit 60 to press the locking pin 40 against the surface of the human tissue, where the locking pin 40 is located after the locking process is completed; this step is important and is extremely critical to ensure the effectiveness of suturing, because the tension of the suture 50 locked in this position will not change, while when the locking pin 40 is not properly pressed against the surface of the human tissue, the suture 50 may loose after the locking is completed and can be prevented only after the locking pin 40 is properly pressed against the surface of the human tissue;

S5: providing a pressing power to the clamping structure 20 through the power rod 30 to enable the locking pin 40 to clamp the suture 50, wherein this process requires the operator to apply a force to the power rod 30 outside the human body; and S6: cutting the suture 50 and removing from the human body the hooking assembly 10 separated from the suture 50, excess suture 50 and the locking device.

The control of the end of the suture 50 may be implemented in the following two ways.

Figure 19:
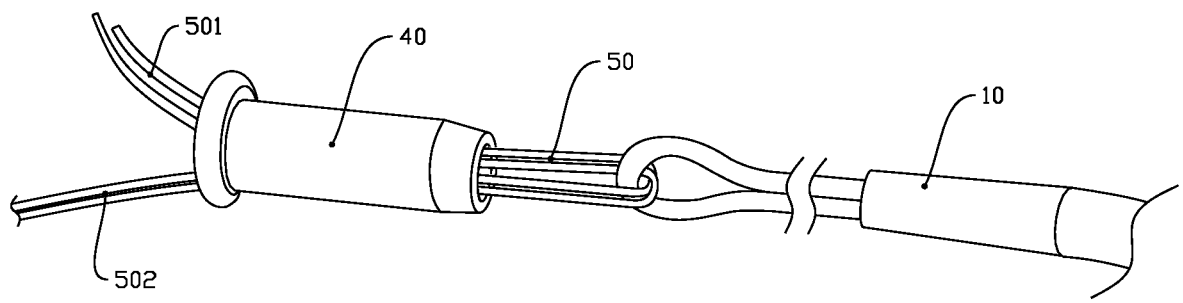
FIG. 19 is a schematic diagram of the position of the suture deviating from the end overlapping and penetrating the through area of the locking pin.

As shown in FIG. 19, the first way of controlling the end of suture 50 includes pulling the end of suture 50 on the side of the locking pin 40 proximate to the sutured tissue such that during the pulling of the force application end 102, the suture 50 deviating from the end overlaps and penetrates through the through area 401 of the locking pin 40.

In this case, the end 501 of the suture 50 and the end 502 of the suture 50 leading out from the tissue are located on one side of the locking pin 40, wherein the end 501 is controlled by an instrument and the end 502 leading out from the tissue is restricted by the tissue. In this process, the suture 50 is pulled by the force application end 102, causing the suture 50 to form a portion in which the suture is overlapped and doubled and which is finally pressed and fixed in the through area 401 of the locking pin 40. In this way, the number of sutures 50 inside the locking pin 40 is increased, making the pressing more stable, and the end 501 is fixed by the instrument throughout the process, effectively avoiding the problem of loosening of the suture 50. However, in this way, the size of the through area 401 of the locking pin 40 may be relatively large.

Figure 20:
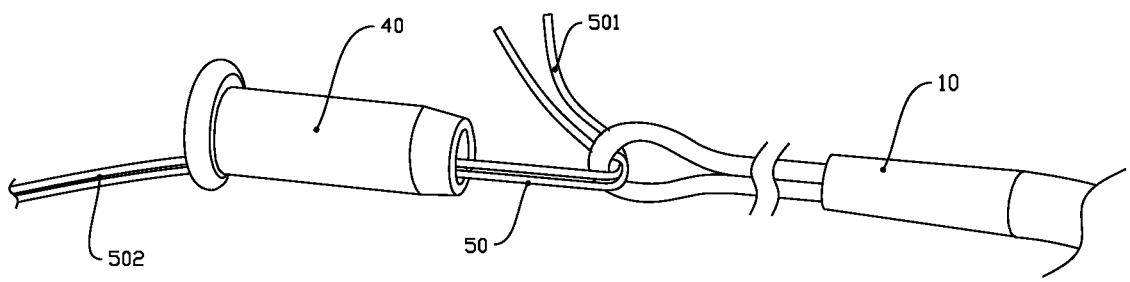
FIG. 20 is a schematic diagram of the end of the suture penetrating the through area of the locking pin.

As shown in FIG. 20, the second way of controlling the end of suture 50 includes pulling the force application end 102 to drive the end 501 of suture 50 through the through area 401 of the locking pin 40 by the annular structure 102, and pulling the end of suture 50 on the side of the locking pin 40 away from the sutured tissue.

Here, the end 501 refers to the most marginal part of the end having a certain length range of the suture 50. The end 501 of the suture 50 passes completely through the through area 401, and after this process is completed, the suture 50 can be pulled on the other side of the locking pin 40. The size of the locking pin 40 can be reduced because the number of sutures 50 passing through the locking pin 40 in this process is small. During the process of the end 501 passing through the through area 401, the suture 50 may be loosened to a certain extent, but it can be pulled again later by pulling the end.

The above two ways are within the protection scope of the present invention and can be selected according to actual needs.

The minimally invasive surgical suture end locking device according to the present invention can work when installed onto an operating gun, as detailed in the following embodiments.

Figure 21:
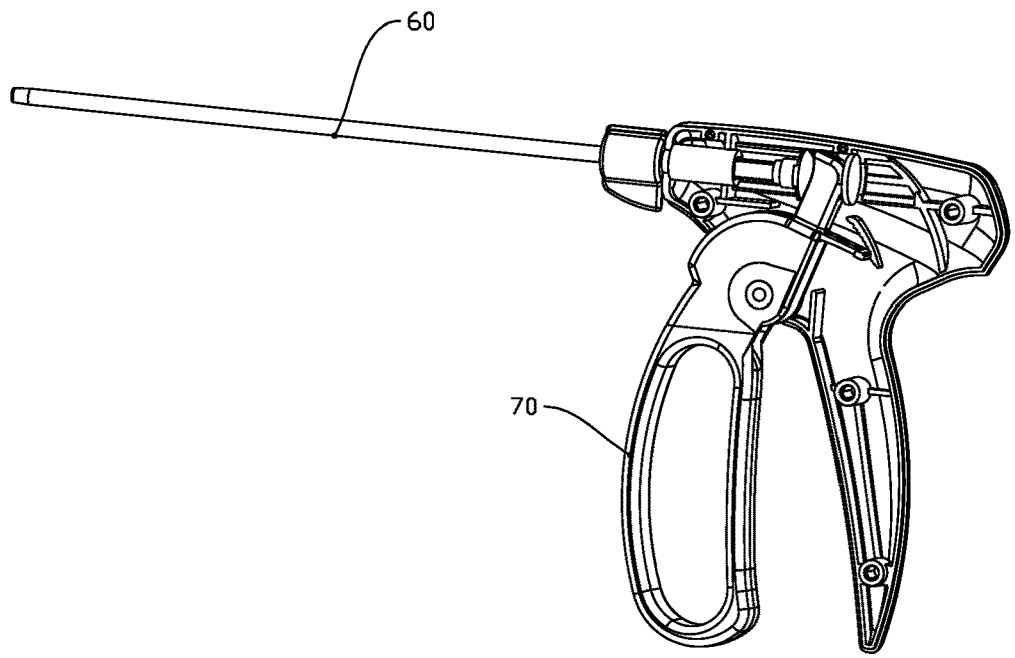
FIG. 21 is a schematic diagram of the structure of a minimally invasive surgical suture end locking operating gun (only one half-shell is shown)
Figure 22:
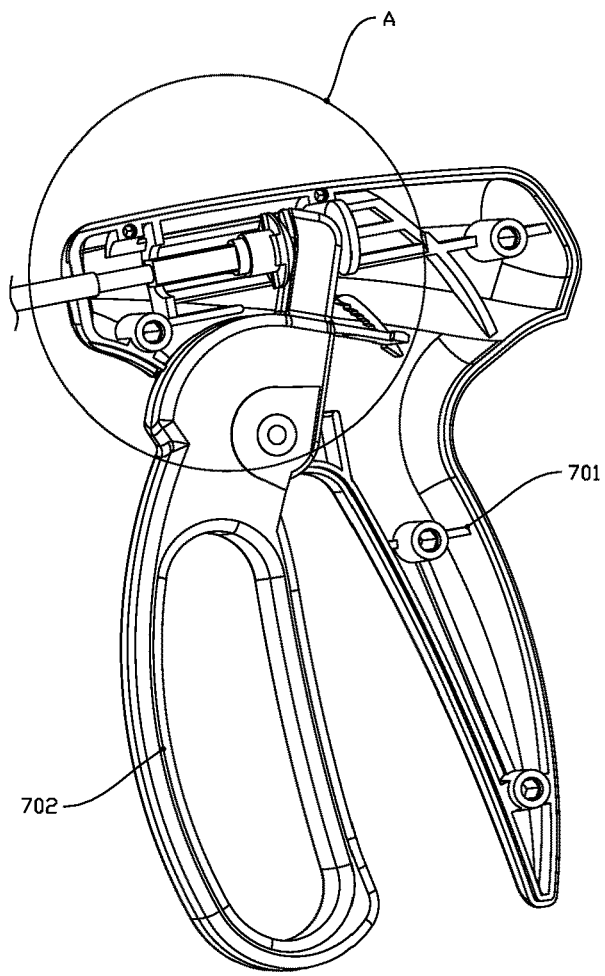
FIG. 22 is a partially enlarged view of the half-shell at the position where it is connected to the force application handle.
Figure 23:
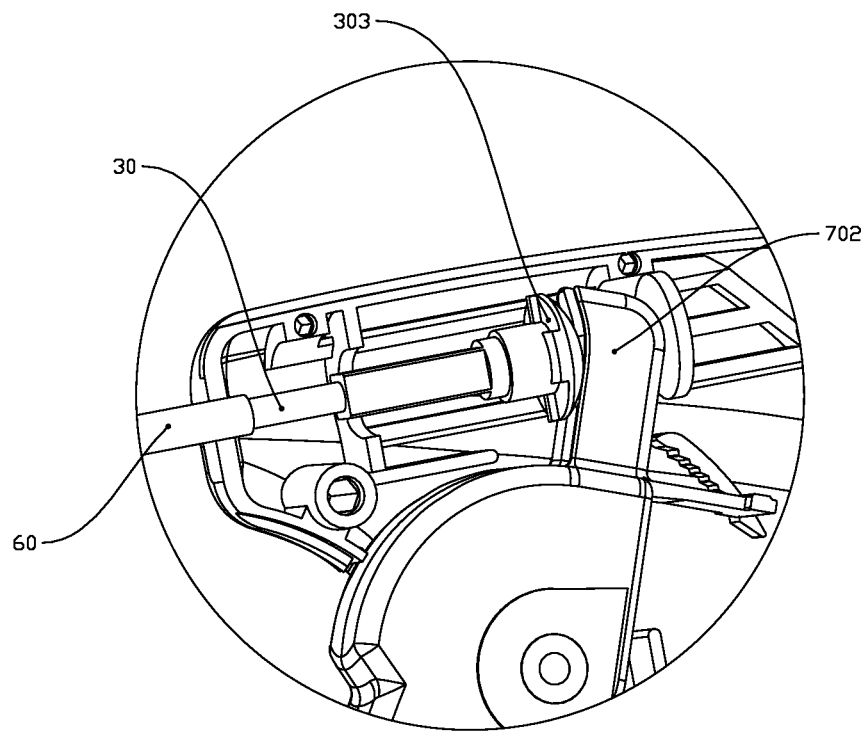
FIG. 23 is a partially enlarged view at A in FIG. 22.

As shown in FIGS. 21 to 23, there is provided a minimally invasive surgical suture end locking operating gun, comprising the minimally invasive surgical suture end locking device described above and an operating assembly disposed outside the human body for operation.

The operating assembly 70 comprises two half-shells 701 assembled in a docking manner to form a cavity, and a force application handle 702 partially disposed within the cavity and rotatably connected to the half-shells 701, wherein one end of the force application handle 702 located within the cavity is slidably connected to the power rod 30, wherein the outer cross-section of the external conduit 60 is a cylinder having an axis fixed relative to the half-shells 701, and wherein the force application handle 702 presses the power rod 30 during rotation.

The two half-shells 701 are docked by the existing fixing method, and the docking here may be done in a detachable manner, so as to facilitate the observation of the internal structure, etc. For the rotational connection between the force application handle 702 and the half-shells 701, it can be implemented by arranging a shaft body on the force application handle 702 and a hole for insertion of the shaft body on the half-shells 701, so that the force application handle 702 can be naturally fixed during the docking and assembling process of the two half-shells 701. The force application handle 702 may be an integral structure or an assembled structure, which can be selected according to the actual production needs.

Figure 24:
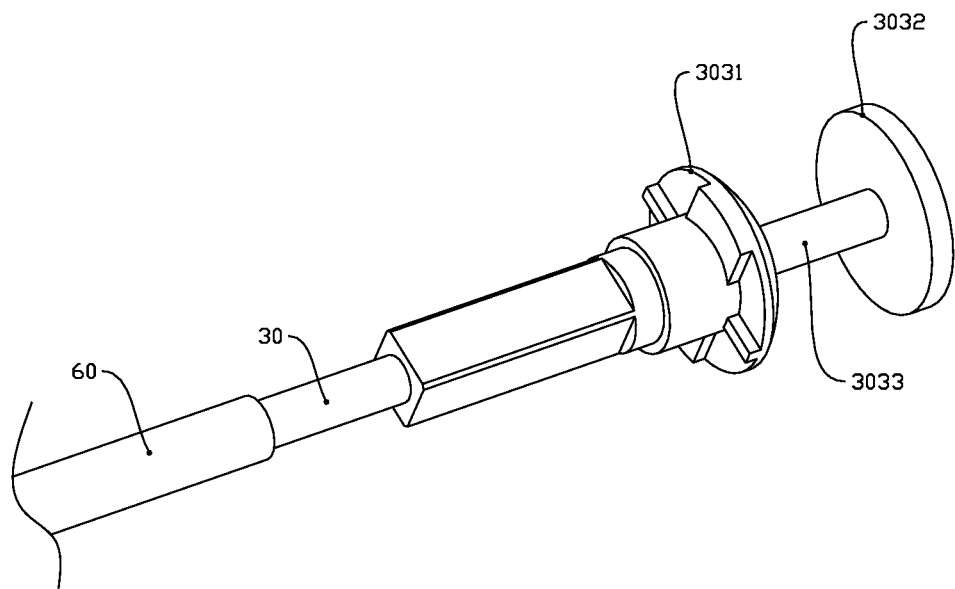
FIG. 24 is a schematic diagram of the location and structure of the connecting structure.
Figure 25:
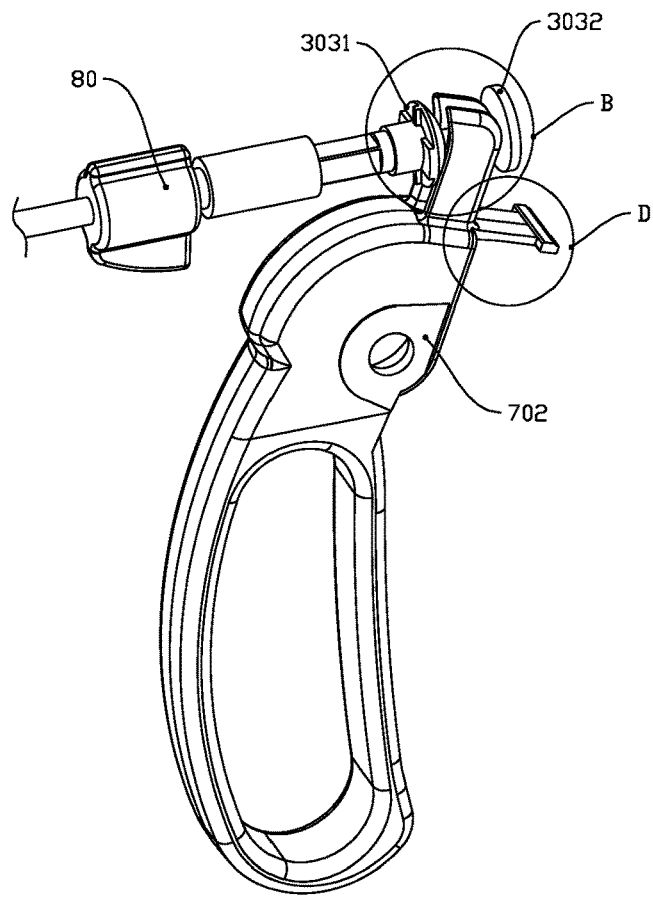
FIG. 25 is a partially enlarged view of the connecting structure at the position where it is connected to the force application handle.

During operation, the power rod 30 is pressed by controlling the counterclockwise rotation of the force application handle 702 as shown in FIGS. 22 and 23. When the force application handle 702 moves in the opposite direction, the pressure is naturally released, whereby the removal of the locking pin 40 from the external conduit 60 can be realized. In order to reduce the force on the locking pin 40 during the above removal process, as shown in FIGS. 24 and 25, the end of the power rod 30 is provided with a connecting structure 303 slidably connected with the force application handle 702.

The connection structure 303 comprises a first stop 3031 and a second stop 3032 provided side by side along the length of the power rod, the first stop 3031 and the second stop 3032 being connected to each other by a connecting rod 3033 that may be arranged to be parallel with the power rod 30. The force application handle 702 is provided with a recess 7021 at an end thereof to accommodate the connecting rod 3033, the end of the force application handle 702 being affixed to the first stop 3031 and second stop 3032, respectively, wherein the first stop 3031 is relatively close to the minimally invasive surgical suture end locking device.

In this way, reverse rotation is achieved by the force application handle 702 pressing the connecting structure 303, so that the power rod 30 can be driven to reset when the power rod 30 is released from pressing the clamping structure 20. Therefore, the clamping structure 20 in contact with the locking pin 40 is no longer subjected to the pressing force, which facilitates the removal of the locking pin 40 relative to the external conduit 60.

Figure 26:
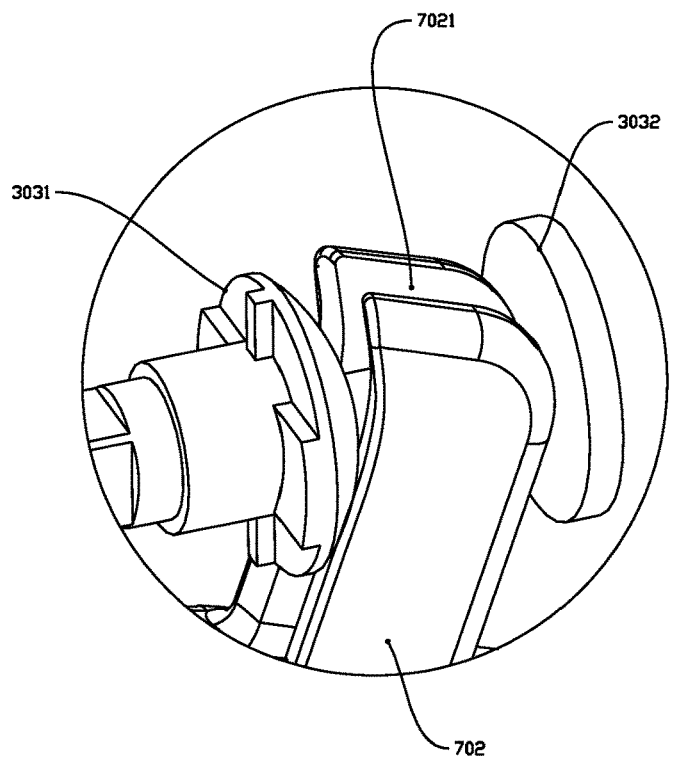
FIG. 26 is a partially enlarged view at B in FIG. 25.

As a preferred embodiment, as shown in FIG. 26, the first stop 3031 is in contact with the force application handle 702 through a spherical surface, and the force application handle 702 is correspondingly provided with a curved surface that is curved in the same direction to fit the spherical surface. The fitting between the spherical surface and the curved surface makes sliding smoother and reduce the friction surface damage caused by hard friction during the sliding process of the force application handle 702 relative to the first stop 3031. The spherical surface may be one of a spherical or ellipsoidal surface, but is preferably a regular surface, so as to facilitate the machining. The curved surface on the force application handle 702 may be arranged to follow the curved form of the spherical surface, and may be formed synchronously with the force application handle 702 or obtained by subsequent machining.

As a preferred embodiment, the force application handle 702 is in contact with the second stop 3032 through the curved surface. However, there is no additional machining requirement for the second stop 3032, because the pressing force between the force application handle 702 and the second stop 3032 is small during the return stroke of the force application handle 702. Therefore, the purpose of smooth sliding between the two can be completely satisfied by the curved surface of the force application handle 702, thereby reducing the machining difficulty of the second stop 3032. The stop 3032 is formed as a circular piece, and a blocking structure is provided inside the cavity to limit the limit position of the return stroke. The combined structure composed of the first stop 3031, the second stop 3032 and the connecting rod 3033 can be integrally formed, and after being independently machined, connected to the main body of the power rod 30 to obtain the complete structure of the power rod 30. This way is relatively simple and the shape is easier to control.

As a preferred embodiment, the minimally invasive surgical suture end locking operation gun further comprising a rotating structure 80 having a first end 801 jacketed on the external conduit 60 and located outside the cavity and fixedly connected to the external conduit 60, and a second end 802 jacketed on the power rod 30 and located inside the cavity and driving the power rod 30 to rotate.

Figure 27:
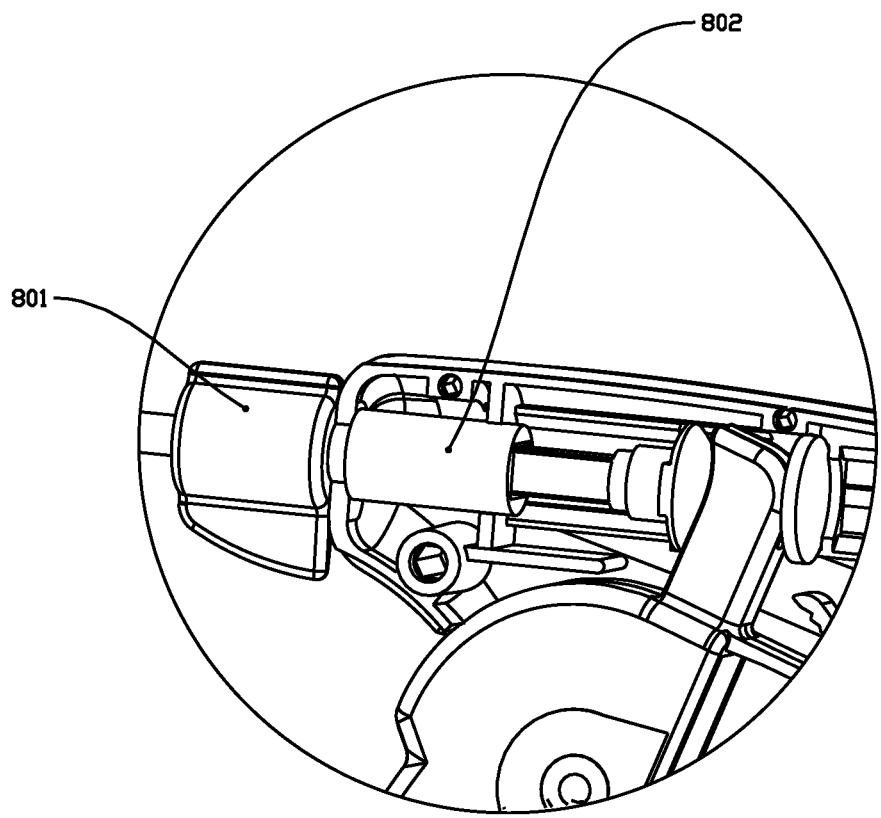
FIG. 27 is a schematic diagram of the position and structure of the rotating structure.

During the locking operation through the operating gun, due to the limited space inside the human body, in order to avoid the human tissue structure, the opening direction of the through hole 601 of the external conduit 60, that is, the leading out direction of the force application end 102, has many possibilities. In order to accommodate such possibilities and facilitate the control of the opening direction of the through hole 601, as shown in FIG. 27, a rotating structure 80 is provided. Through the control of the first end 801, the operator rotates the external conduit 60. Of course, during the rotation, the external conduit 60 only rotates around a fixed rotation axis, without moving in the axial direction and the radial direction. During the rotation, the second end 802 moves synchronously with the first end 801, thereby driving the power rod 30 to rotate synchronously, but the rotation here does not affect the movement of the power rod 30 along the length direction. During the rotation, the rotation is made smoother through cooperation with the above optimized structure in which the first stop 3031 contacts with the force application handle 702 through the spherical surface.

A snap slot is provided between the first end 801 and the second end 802 to accommodate a partial edge of the half-shells 701, thereby acting as a limiter, making the installation of the entire rotating structure 80 easier. The second end 802 is affixed to the power rod 30 through a prismatic through hole to realize transmission of rotational power. A local part of the power rod 30 cooperating with the prismatic through hole is a corresponding prismatic structure that be integrally formed with the structure including the first stop 3031, the second stop 3032 and the connecting rod 3033 in the above preferred embodiment and both structures, as a whole, are fixedly connected with the end of the main body of the power rod 30 to facilitate machining.

Figure 28:
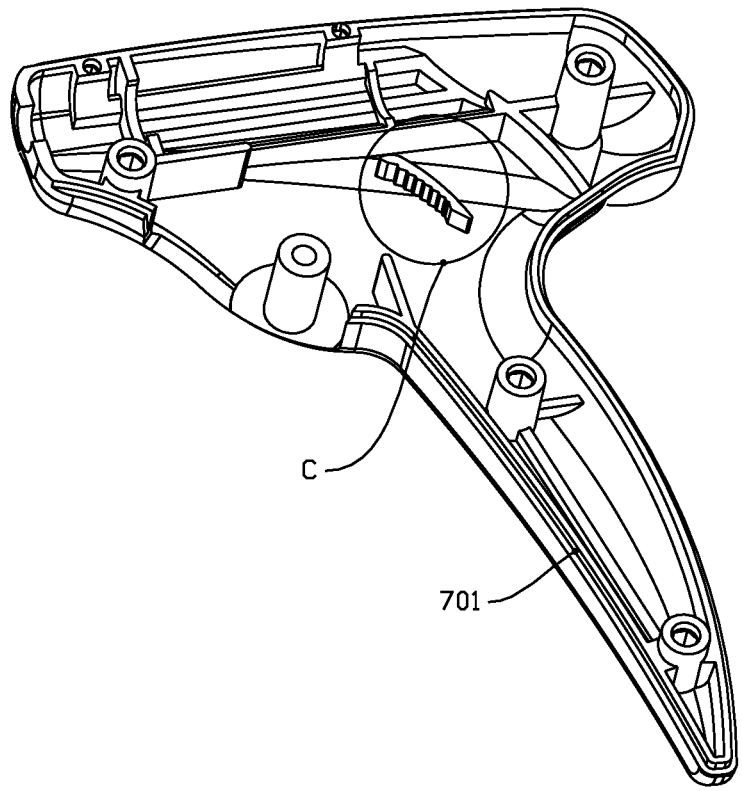
FIG. 28 is a schematic structural diagram of the half-shell.
Figure 29:
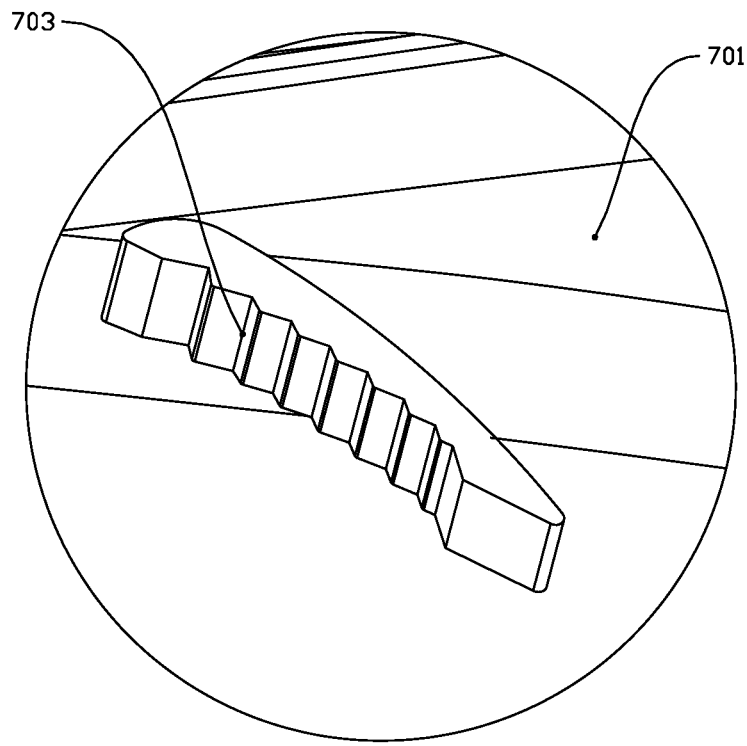
FIG. 29 is a partially enlarged view at C in FIG. 28.
Figure 30:
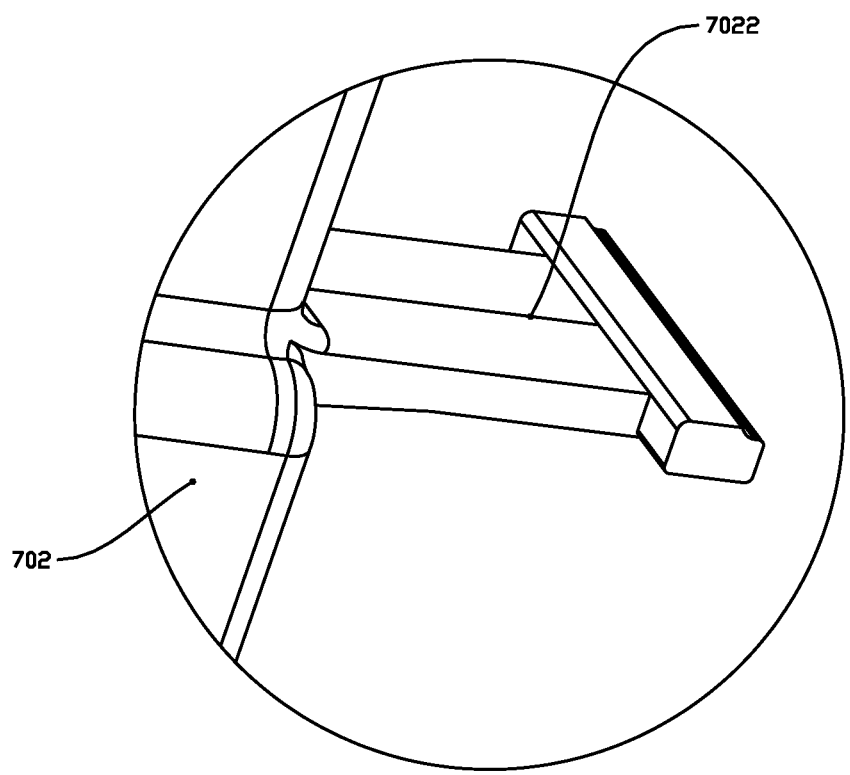
FIG. 30 is a partially enlarged view at D in FIG. 25.

As a preferred embodiment, the operating gun further comprises a sensing structure, as shown in FIGS. 28 to 30, wherein the sensing structure comprises a rod body 7022 leading out from the force application handle 702, and a stepped seat 703 disposed on the inner wall of the cavity and having a plurality of stepped structures, wherein the rod body 7022 is arranged against the stepped seat, so that it sequentially reaches different stepped structures on the stepped seat 703 during rotation of the force application handle 702, creating a jamming feeling which is transmitted to the operator through the force application handle 702. With this structural form, the operator can perceive the operation process through the frequency and number of occurrences of the jamming feeling during the operation, thereby making the control more precise.

The basic principles, main features and advantages of the present invention have been shown and described above. Those skilled in the industry should understand that the present invention is not limited by the foregoing embodiments. The foregoing embodiments and descriptions only illustrate the principles of the present invention. Without departing from the spirit and scope of the present invention, the present invention will have various changes and improvements, which fall within the scope of the claimed invention. The scope of protection claimed by the present invention is defined by the appended claims and their equivalents.

The invention claimed is:

1. A minimally invasive surgical suture end locking device for clamping and securing the end of a suture by means of a locking pin, comprising: a hooking assembly, a clamping structure, a power rod and an external conduit;
   wherein the hooking assembly comprises an annular structure enclosed by a flexible material and a force application end leading out relative to the annular structure, wherein the annular structure is configured to lead out from a through area of the locking pin with a lead-out portion forming a closed area, and wherein the force application end is configured to drive the suture entering the closed area partially through the through area by pulling the annular structure under the action of an external force in the human body;
   wherein the clamping structure is configured to press the locking pin so that the locking pin deforms and clamps the suture, and wherein the power rod is provided with a pressing portion to press the clamping structure by linear motion so that the clamping structure moves and completes the pressing action; and
   wherein the clamping structure and the power rod are disposed in the external conduit, wherein the locking pin is inserted from an end of the external conduit and the depth of insertion is limited by a stop structure provided on the locking pin, and wherein the external conduit is provided with a through hole through which a portion of the suture passing through the through area is led out by the pulling of the annular structure, the through hole being provided on the side of a position where the clamping structure and the power rod contact each other at a set distance from the contact position;
   wherein the external conduit comprises a guide seat mounted at an end thereof, wherein the guide seat is configured to limit the insertion depth of the locking pin and guide the movement of the clamping structure; and wherein the guide seat is provided with a guide groove, and the clamping structure is provided with a protruding portion moving along the guide groove.

2. The minimally invasive surgical suture end locking device according to claim 1, wherein the through hole is a straight hole and extends along the linear movement direction of the power rod.

3. The minimally invasive surgical suture end locking device according to claim 1, wherein the force application end is a hook structure.

4. The minimally invasive surgical suture end locking device according to claim 1, wherein the power rod is provided with a cutting portion at an end thereof, wherein the cutting portion approaches one sidewall of the through hole along with the pressing movement of the power rod until it reaches a close enough distance with respect to the one sidewall of the through hole and continues to approach, the cutting portion thus cutting the suture passing through the through hole by cooperating with the edge of the sidewall.

5. The minimally invasive surgical suture end locking device according to claim 1, wherein the movement of the clamping structure is perpendicular to the direction of insertion of the locking pin into the guide seat.

6. The minimally invasive surgical suture end locking device according to claim 1, wherein the clamping structure is provided with at least one raised structure facing the locking pin for partially pressing the locking pin.

7. The minimally invasive surgical suture end locking device according to claim 1, wherein the pressing portion comprises a slope for pressing the clamping structure, wherein an end of the slope forms a sharp structure that can be inserted into a gap between the clamping structure and the inner wall of the external conduit, and wherein the slope is inclined relative to the direction in which the guide seat guides the clamping structure.

8. A minimally invasive surgical suture end locking method using the minimally invasive surgical suture end locking device according to claim 1, comprising the following steps of:
    installing the hooking assembly in place relative to the locking pin and installing the locking pin in place relative to the external conduit, and extending the hooking assembly and the locking pin into a designated position within the human body;
    pulling the end of suture after suturing is complete so that the end of suture enters the closed area;
    pulling the force application end and controlling the end of suture so that the suture partially penetrates the through area with a preset range of tension being maintained;
    controlling the external conduit to press the locking pin against the surface of the human tissue;
    providing pressing power to the clamping structure through the power rod to enable the locking pin to clamp the suture; and
    cutting the suture and removing from the human body the hooking assembly separated from the suture, excess suture and locking device.

9. The minimally invasive surgical suture end locking method according to claim 8, wherein controlling the end of suture includes pulling the suture end on the side of the locking pin proximate to the sutured tissue such that during the pulling of the force application end, the suture deviating from the end overlaps and penetrates through the through area of the locking pin.

10. The minimally invasive surgical suture end locking device according to claim 8, wherein controlling the end of suture includes pulling the force application end to drive the suture end through the through area of the locking pin by the annular structure, and pulling the suture end on the side of the locking pin away from the sutured tissue.

11. A minimally invasive surgical suture end locking operating gun, comprising the minimally invasive surgical suture end locking device according to claim 1 and an operating assembly disposed outside the human body for operation, wherein the operating assembly comprises two half-shells assembled to in a docking manner to form a cavity, and a force application handle partially disposed within the cavity and rotatably connected to the half-shells; and
wherein one end of the force application handle located within the cavity is slidably connected to the power rod, wherein the outer cross-section of the external conduit is a cylinder having an axis fixed relative to the half-shells, and wherein the force application handle presses the power rod during rotation.

12. The minimally invasive surgical suture end locking operating gun according to claim 11, wherein an end of the power rod is provided with a connection structure slidably connected to the force application handle, the connection structure comprising:
    a first stop and a second stop provided side by side along the length of the power rod, the first stop and the second stop being connected to each other by a connecting rod, the first stop being relatively close to the minimally invasive surgical suture end locking device;
    wherein the force application handle is provided with a recess at an end thereof to accommodate the connecting rod, the end of the force application handle being affixed to the first stop and second stop, respectively.

13. The minimally invasive surgical suture end locking operating gun according to claim 12, wherein the first stop is in contact with the force application handle by means of a spherical surface, and the force application handle is correspondingly provided with a curved surface that is curved in the same direction to fit with the spherical surface.

14. The minimally invasive surgical suture end locking device according to claim 12, wherein the force application handle is in contact with the second stop by means of a curved surface.

15. The minimally invasive surgical suture end locking operating gun according to claim 11, further comprising a rotating structure having a first end jacketed on the external conduit and located outside the cavity and fixedly connected to the external conduit, and a second end jacketed on the power rod and located inside the cavity and driving the power rod to rotate.

16. The minimally invasive surgical suture end locking operating gun according to claim 15, wherein a snap slot is provided between the first end and the second end for accommodating a partial edge of the half-shells.

17. The minimally invasive surgical suture end locking device according to claim 15, wherein the second end is affixed to the power rod through a prismatic through hole to realize transmission of rotational power.

18. The minimally invasive surgical suture end locking operating gun according to claim 11, further comprising a sensing structure, wherein the sensing structure comprises a rod body leading out from the force application handle, and a stepped seat disposed on the inner wall of the cavity and having a plurality of stepped structures; and
    wherein the rod body is arranged against the stepped seat, so that it sequentially reaches different stepped structures on the stepped seat during rotation of the force application handle, creating a jamming feeling which is transmitted to the operator through the force application handle.

* * * * *